(12) United States Patent
Murray et al.

(10) Patent No.: US 7,387,773 B2
(45) Date of Patent: Jun. 17, 2008

(54) VACCINE

(75) Inventors: Alan Murray, Palmerston North (NZ); Christine Dupont, Palmerston North (NZ); Jeremy Lawrence Rae, Tauranga (NZ)

(73) Assignees: Massey University, Palmerston North (NZ); The New Zealand Meat Board, Wellington (NZ); Wool Production Technologies Ltd, Wellington (NZ)

( * ) Notice: Subject to any disclaimer, the term of this patent is extended or adjusted under 35 U.S.C. 154(b) by 0 days.

(21) Appl. No.: 10/486,270

(22) PCT Filed: Aug. 7, 2002

(86) PCT No.: PCT/NZ02/00152

§ 371 (c)(1),
(2), (4) Date: Aug. 24, 2004

(87) PCT Pub. No.: WO03/013596

PCT Pub. Date: Feb. 20, 2003

(65) Prior Publication Data

US 2005/0025783 A1    Feb. 3, 2005

(30) Foreign Application Priority Data

Aug. 7, 2001    (NZ) ..................... 513418

(51) Int. Cl.
| | |
|---|---|
| *A61K 49/00* | (2006.01) |
| *A61K 39/00* | (2006.01) |
| *A61K 39/02* | (2006.01) |
| *A61K 39/04* | (2006.01) |
| *A01N 63/00* | (2006.01) |
| *C12P 1/00* | (2006.01) |
| *C12N 9/92* | (2006.01) |

(52) U.S. Cl. ..................... 424/9.2; 424/9.1; 424/93.1; 424/184.1; 424/234.1; 424/248.1; 435/41; 435/243

(58) Field of Classification Search ................ 424/9.1, 424/9.2, 93.1, 184.1, 234.1, 248.1; 435/41, 435/243
See application file for complete search history.

(56) References Cited

U.S. PATENT DOCUMENTS 6,277,580 B1   8/2001   Ellingson et al. .............. 435/6
6,387,372 B1   5/2002   Cocito et al. ............... 424/185

FOREIGN PATENT DOCUMENTS

DE    19728834    1/1999

OTHER PUBLICATIONS

Derwent Abstract Acces No. 90-171668/23, BE 1002-022 A (ANDA Biologicals) May 22, 1990.
Valentin-Weigand et al, J Vet Mded B, vol. 39, 1992, pp. 762-766 Protein Antigens Secreted by Mycobacterium paratuberculosis.
Derwent Abstract Acces No. 2002-247253/30, JP 2001342147 A (Momotani E) Dec. 11, 2001.
Beeman et al, The Compendium, vol. 11, No. 11, pp. 1415-1421, 1989, Johne's Disease (Paratuberculosis) in Sheep.

*Primary Examiner*—Rodney P Swartz
(74) *Attorney, Agent, or Firm*—Jacobson Holman PLLC (57) ABSTRACT

The invention provides a vaccine comprising secreted protein derived from *Mycobacterium avium* subsp *paratuberculosis* (*M. ptb*) substantially free of whole organisms of that species either dead or alive. The secreted protein may be obtained from a culture of *M. ptb* with the microorganisms being removed by centrifugation and subsequent filtration. The vaccine may be used for vaccination against Johne's disease.

10 Claims, 7 Drawing Sheets

FIGURE 1

| Lane | | |
|---|---|---|
| 1. | Biorad Precision protein Standard | |
| 2. | 20µg growth medium | |
| 3. | 20µg of M.ptb culture filtrate (CF) | |
| * | Major M.ptb protein bands | |
| + | Albumin band | |

VACCINE

This is a nationalization of PCT/NZ02/00152 filed Aug. 7, 2002 and published in English.

TECHNICAL FIELD

This invention relates to vaccines comprising proteins from *Mycobacterium avium* subsp *paratuberculosis*.

BACKGROUND ART

Johne's disease (paratuberculosis) is a chronic, contagious infection with the acid-fast-staining bacillus *Mycobacterium avium* subsp *paratuberculosis* (*M. ptb*). The disease affects ruminants and is characterized by emaciation and intermittent diarrhoea or softening of faeces. Johne's disease is a major disease of cattle, sheep, goats, deer, and camels (Beeman et al, The Compendium 11,1415 (1989)).

The currently favoured treatment is with a living vaccine (Neoparasec, Merial). This vaccine contains live organisms of the Weybridge strain, an attenuated strain of *M. ptb*. Killed vaccines are also known.

The existing vaccines have two disadvantages. Carcasses of animals treated with the vaccines contain whole organisms which are not readily distinguishable from tuberculosis organisms. In addition both types of vaccines leave injection site lesions which can be easily confused with tuberculosis lesions.

An object of the present invention is to prepare a vaccine against Johne's disease in which the above disadvantages are either not present or are reduced.

DISCLOSURE OF THE INVENTION

In one aspect the invention provides a vaccine comprising secreted protein derived from *Mycobacterium aviuni* subsp *paratuberculosis* (*M. ptb*) which is substantially free of whole organisms of that species either dead or alive. Preferably there are no organisms of *M. ptb*. The vaccine of the invention may be used for treating Johne's disease.

The term "substantially free" indicates that the number of live or dead organisms is too few to have significance in the vaccination process (for example fewer than 1000/ml).

Preferably the secreted proteins are obtained from a culture of *M. ptb*.

Preferably the microorganisms are of an attenuated strain.

Preferably the strain is the Weybridge vaccine strain.

Preferably the vaccine additionally comprises an adjuvant.

Preferably the vaccine comprises a serum albumin, more preferably a heterologous serum albumin. For sheep the currently preferred albumin is bovine serum albumin. For cows use of ovine serum albumin is preferred.

Preferably where the secreted proteins are obtained from a microorganism culture, the microorganisms are removed by centrifugation and subsequently filtered to remove remaining bacteria Preferably the secreted proteins are concentrated using ultrafiltration.

The term "secreted proteins" herein refers to proteins present in the supernatant after centrifugation for 10 min at 10,000 g of a culture of *Mycobacterium avium* subsp *paratuberculosis* organisms. In addition to exported proteins the supernatant includes proteins which have sloughed off the microorganisms or are present in the culture as a result of other causes.

In a second aspect the invention provides a vaccine against Johne's disease comprising a supernatant of a *Mycobacterium avium* subsp *paratuberculosis* culture which does not contain whole organisms of that species, either dead or alive.

In a third aspect the invention provides a use of a supernatant as defined in the second aspect for the preparation of a medicament for vaccinating an animal against *Mycobacterium avium* subsp *paratuberculosis*.

In a fourth aspect the invention provides a method for vaccinating an animal against *Mycobacterium avium* subsp *paratuberculosis* comprising administering a vaccine of the invention to the animal. Preferably the vaccination is against Johne's disease. Animals for which the method of the invention is particularly useful include ruminants, especially sheep.

EXAMPLES

The following Examples further illustrate practice of the invention.

Example I

Studies were performed with three-month old male neutered Romney lambs obtained from Massey Agricultural Services, Palmerston North, New Zealand. The animals were kept on farming blocks with open grazing and water ad libitum. The sheep used in this study were selected on the basis of negative reactivity with Johnin PPD mycobacterial antigen, as measured by the BOVIGAM (CSL) whole blood IFN-γ assay kit.

CF Antigen

Candidate Johne's vaccine antigen Culture Filtrate (CF), which contains *M. ptb* secreted proteins was prepared from liquid media cultures of *M. ptb* Weybridge vaccine strain (Neoparasec). The cultures were grown to early mid-log phase and the cells removed by centrifugation. The resultant supernatants (containing proteins secreted by *M. ptb*) were filtered to remove remaining bacteria and concentrated approximately 200-fold using ultrafiltration.

CF and Media-only (M) control samples were quantified using a protein assay and diluted appropriately in Phosphate-Buffered Saline (PBS). It is estimated that 5-10% of total CF is *M. ptb* secreted protein, the remainder being bovine serum albumin (BSA).

*M. ptb* Cultures and Quantification of ICD

*M. ptb* Weybridge reference strain 316F was obtained from Rhone-Merieux in freeze-dried form and rehydrated in Middlebrook 7H9 broth (Difco), supplemented with 1 mg/L Mycobactin J (Allied Monitor), 0.2% Bactoglycerol (Difco), 1:100 (v/v) Middlebrook ADC Enrichment (Becton Dickenson) and dextrose to a final concentration of 2 g/L. *M. ptb* was propagated on 7H10 (Difco) agar slopes supplemented with Middlebrook OADC Enrichment as recommended by the manufacturer (Becton Dickenson) and Mycobactin J added as above. Liquid cultures (7H9) were grown at 37° C. with vigorous shaking.

Figure 1:
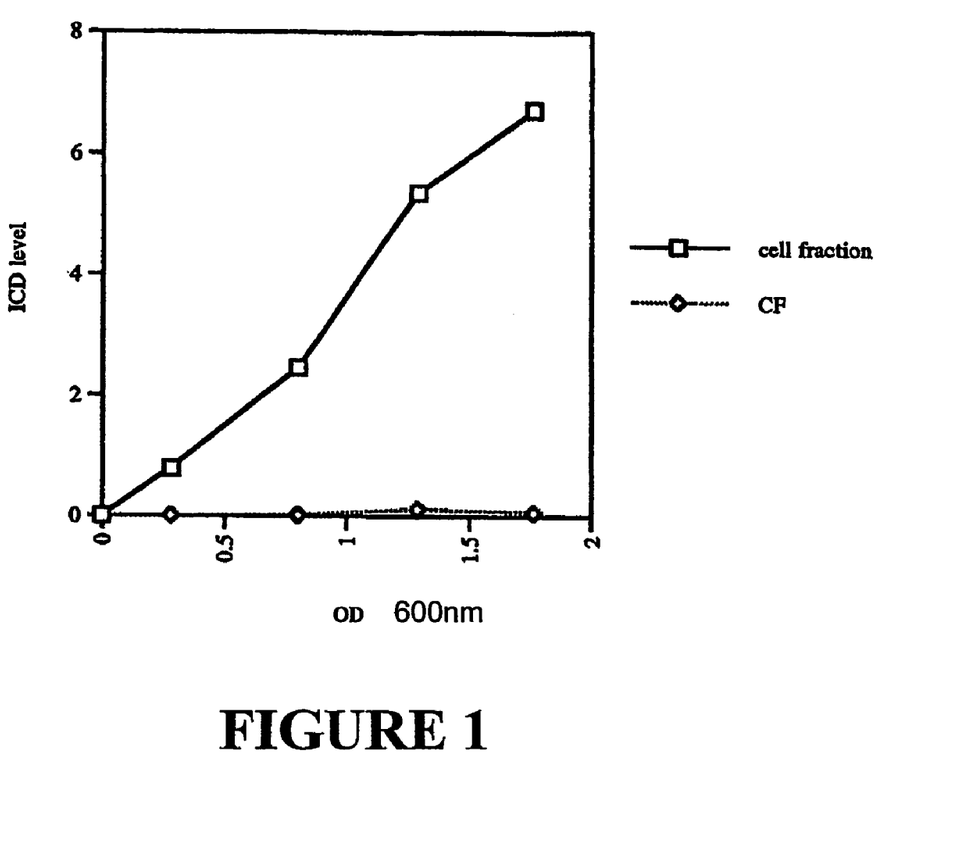
FIG. 1 is graph showing isocitrate dehydrogenase (ICD) in concentrated candidate Johne's vaccine antigen Cell Filtrate (CF) and in cell sonicates plotted against OD600.

The growth of *M. ptb* in liquid medium was monitored by taking Optical Density (OD) readings at 600 nm, at regular intervals for a period of three weeks. The degree of lysis in the cultures was determined by quantification of isocitrate dehydrogenase (ICD), a cytoplasmic marker, in the 200-fold concentrated supernatants (see below). *M. ptb* sonicates were used as positive controls. ICD activity was determined using the ICD diagnostic kit for quantitative determination (Sigma), with changes in absorbance at 340 nm corresponding to the reduction of NADP to NADPH. Results are expressed as international units, which are equal to micromoles of NADPH formed per minute at 25° C. Very little lysis was observed in the preparation of the cell filtrates (see FIG. 1).

Preparation of *M. ptb* Culture Filtrate (CF) Protein

For preparation of culture filtrate, 5 ml of *M. ptb* starter culture was grown to late log phase, innoculated 1:100 into fresh media and grown to mid-log phase (approximately 3 weeks) at 37° C. with vigorous shaking. The cells were removed by centrifugation at approximately 10,000×g and the culture supernatant was passed through a 0.22 μm filter and concentrated by ultrafiltration using an Amicon apparatus containing a 3,000 MW cut-off membrane. The concentrated material was buffer-exchanged by repeated dilutions with PBS buffer and re-concentrated (approx. 1000-fold dilution). For the final concentration step the CF was centrifuged at 3000×g in a Centriplus (Amicon) apparatus with a 3,000 MW cut-off. The resulting 200-fold concentrated CF was stored at −20° C. until required. Protein concentrations were determined using Bio-Rad Protein Assay reagent with bovine serum albumin (BSA) as standard. Control (liquid media only samples) were prepared by filtering and concentrating media as described above.

Figure 2:
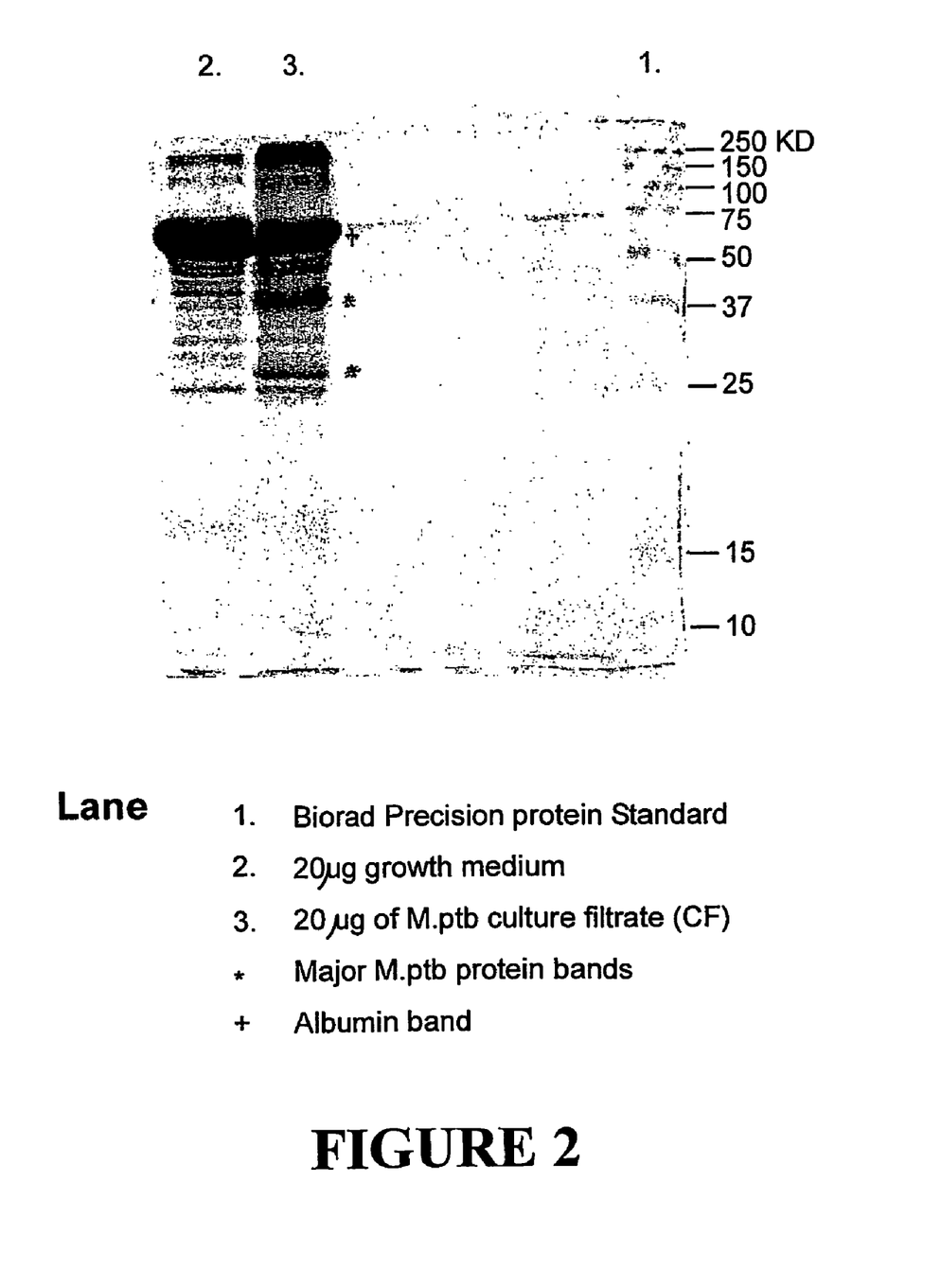
FIG. 2 is a copy of an SDS-PAGE gel of growth medium (lane 2) and CF (lane 3).

FIG. 2 is a copy of an SDS-PAGE gel showing a comparison of the CF proteins (lane 3) with the medium proteins. Major *M. ptb* bands have molecular weights of approximately 27 and 40 KD.

Experimental

A flock of twelve lambs (three months of age) were selected to test the immunogenicity of the CF antigens. Six sheep were vaccinated with the commercial Johue's vaccine Neoparasec (as per the manufacture's instructions). The remaining sheep were kept as non-vaccinated controls. At monthly Intervals blood was obtained from the sheep and tested against candidate vaccine antigens using a BOVIGAM gamma interferon assay kit. Production of gamma interferon by lymphocytes in whole blood is a measure of cell-mediated (protective) immune response to a particular antigen. Each antigen was incubated with 1 ml of blood overnight, then the supernatant was analyzed by BOVIGAM ELISA to determine the levels of gamma interferon produced.

Figure 3:
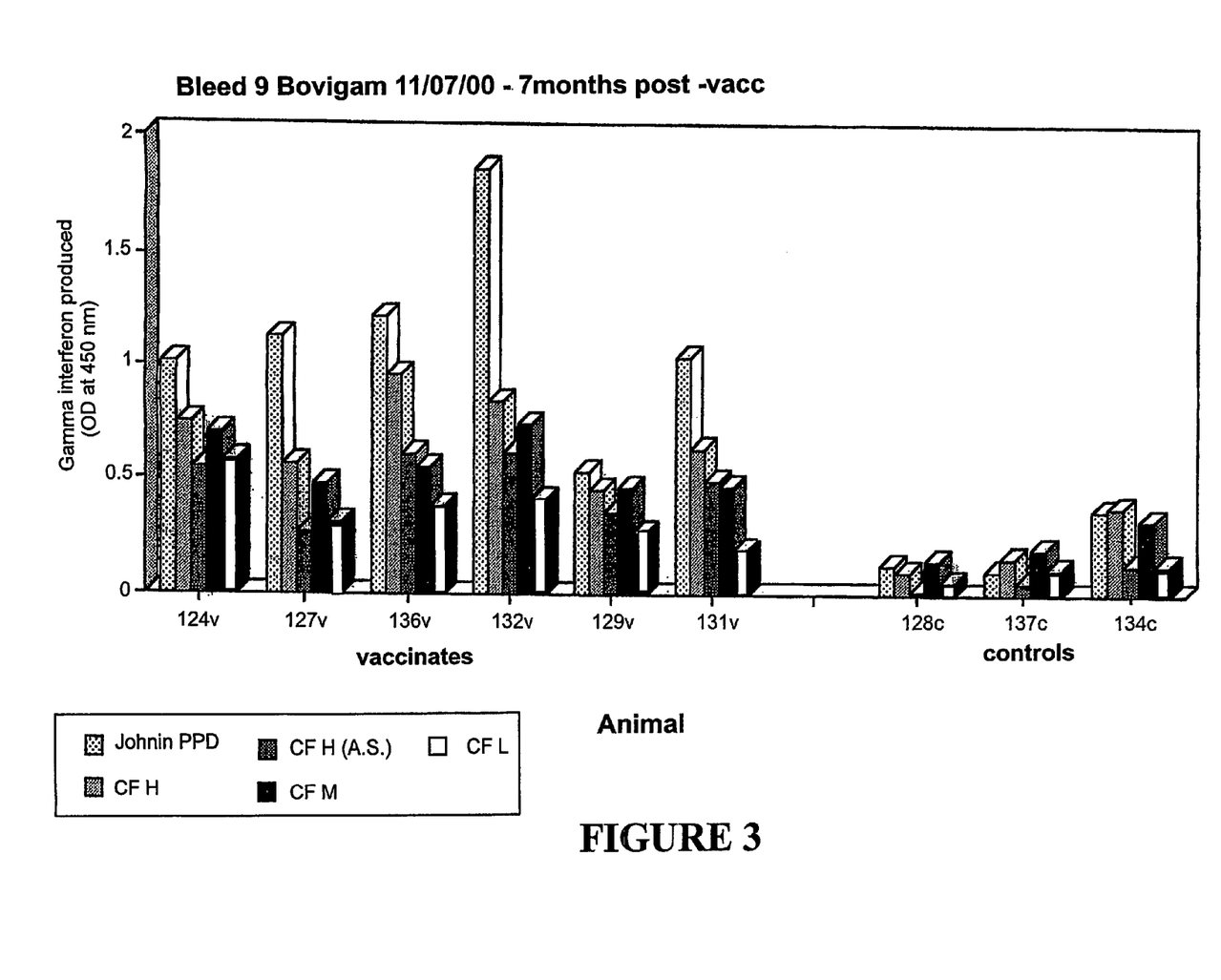
FIG. 3 is a graph showing gamma interferon produced in the blood samples of six vaccinated animals and three control animals in response to Johnin PPD and candidate vaccine antigens.

Six months after vaccination, CF (containing Neoparasec secreted proteins) was included in the monthly bleeds in the following amounts (per 1 ml of sheep blood): H=High=150 μg, M=Medium=75 μg and L=Low=25 μg. Media-only (containing equivalent amounts of media protein) readings were subtracted from the CF readings. In most instances, readings for negative controls did not exceed OD 0.1. Johnin PPD (positive control) was 12.5 μg for all animals. Jobnin PPD is an extract from whole *M. ptb* organisms. PBS served as a negative control for PPD and was subtracted from the PPD readings shown. ODs shown in FIG. 3 are means from triplicate readings (triplicate blood/antigen incubations).

The response to CF was consistently higher in vaccinates that in non-vaccinated control animals. This effect was observed throughout the samples collected in the period 6-10 months. Within animals, response to culture filtrates was shown to be significantly above responses to media controls within vaccinates in almost all cases. Occasionally controls showed significant reactions to Johnin and CF (e.g. 134c, FIG. 3) but this was not consistently observed over different assays.

To provide further evidence that the responses seen resulted from protein antigens in the CF, and not other (non-protein) components CF, protein was precipitated using ammonium sulphate (A.S.) and was included in the 7 month assay. There was still a significant reaction to this fraction, whereas the remaining non-protein supernatant (not shown) gave a very low response. This result indicates that the protein fraction of CF is indeed responsible for the stimulation observed.

CONCLUSIONS

At least part of the "protective type" immune response following Neoparasec vaccination of sheep appears to be due to proteins secreted by the vaccine strain.

Example II

Animals were randomly assigned to four different treatment groups. Group 1 received no vaccination. Group 2 received Neoparasec according to the manufacturer's instructions. Group 3 received CF plus the Neoparasec adjuvant. Group 4 received medium plus Neoparasec adjuvant.

Figure 4:
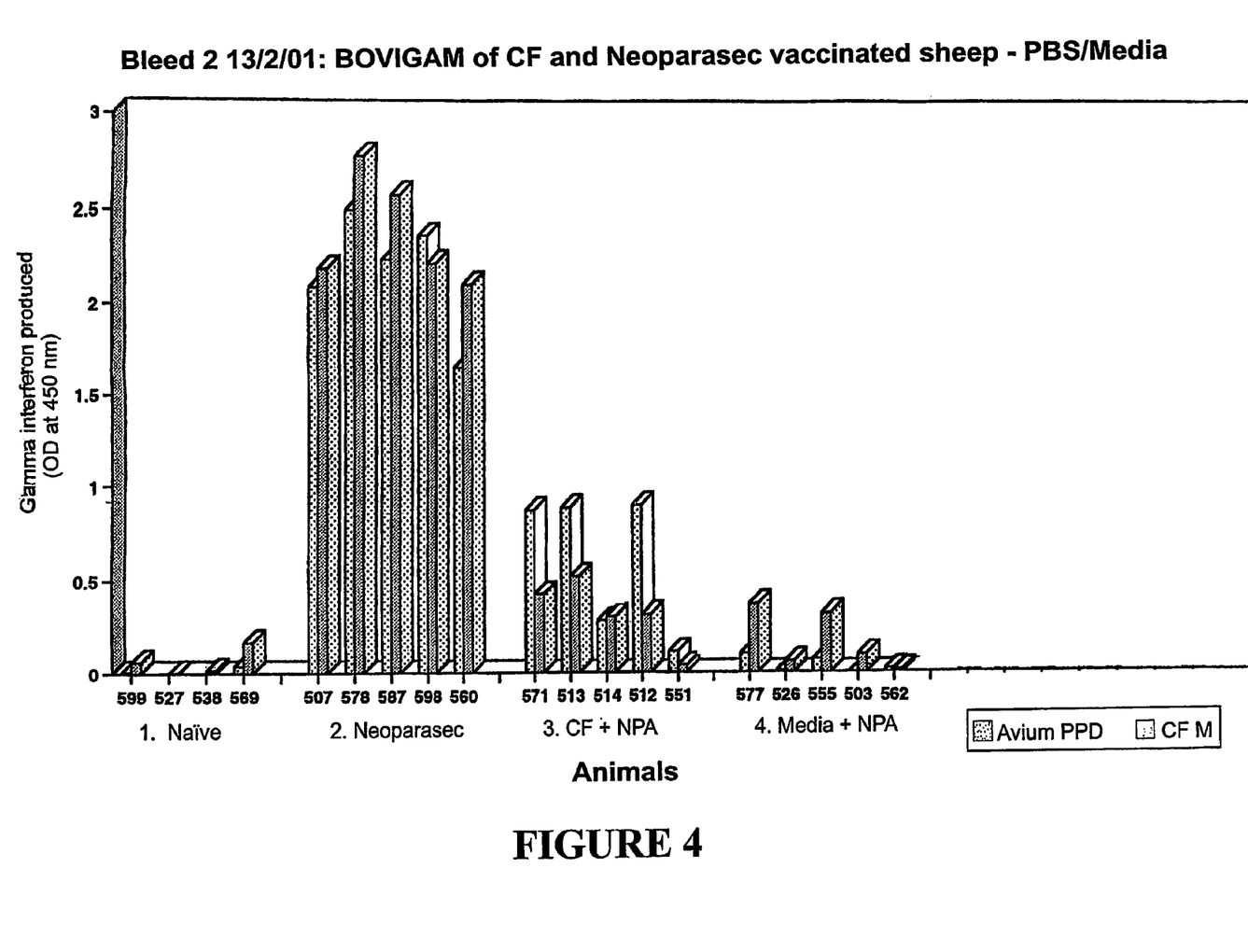
FIG. 4 is a graph showing the interferon produced in blood samples taken from unvaccinated animals and animals vaccinated with Neoparasec, Culture Filtrate (CF) plus Neoparasec Adjuvant (NPA), and media plus NPA, in response to Avium PPD and CF.
Figure 5:
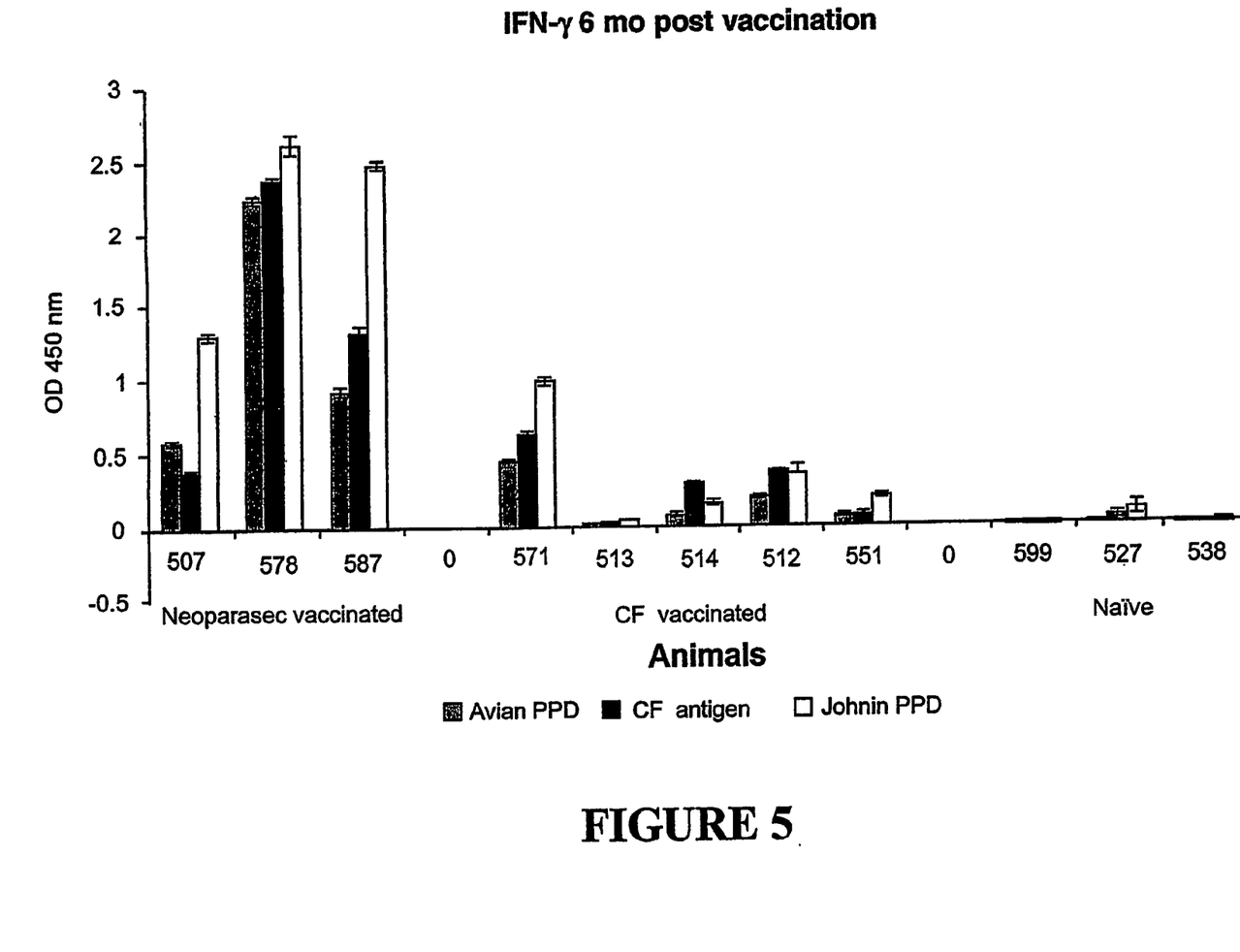
FIG. 5 is a graph showing the interferon produced in blood samples taken from unvaccinated animals and animals vaccinated with Neoparasec and CF plus Neoparasec adjuvant, in response to Avian PPD, Johnin PPD and CF antigen.
Figure 6:
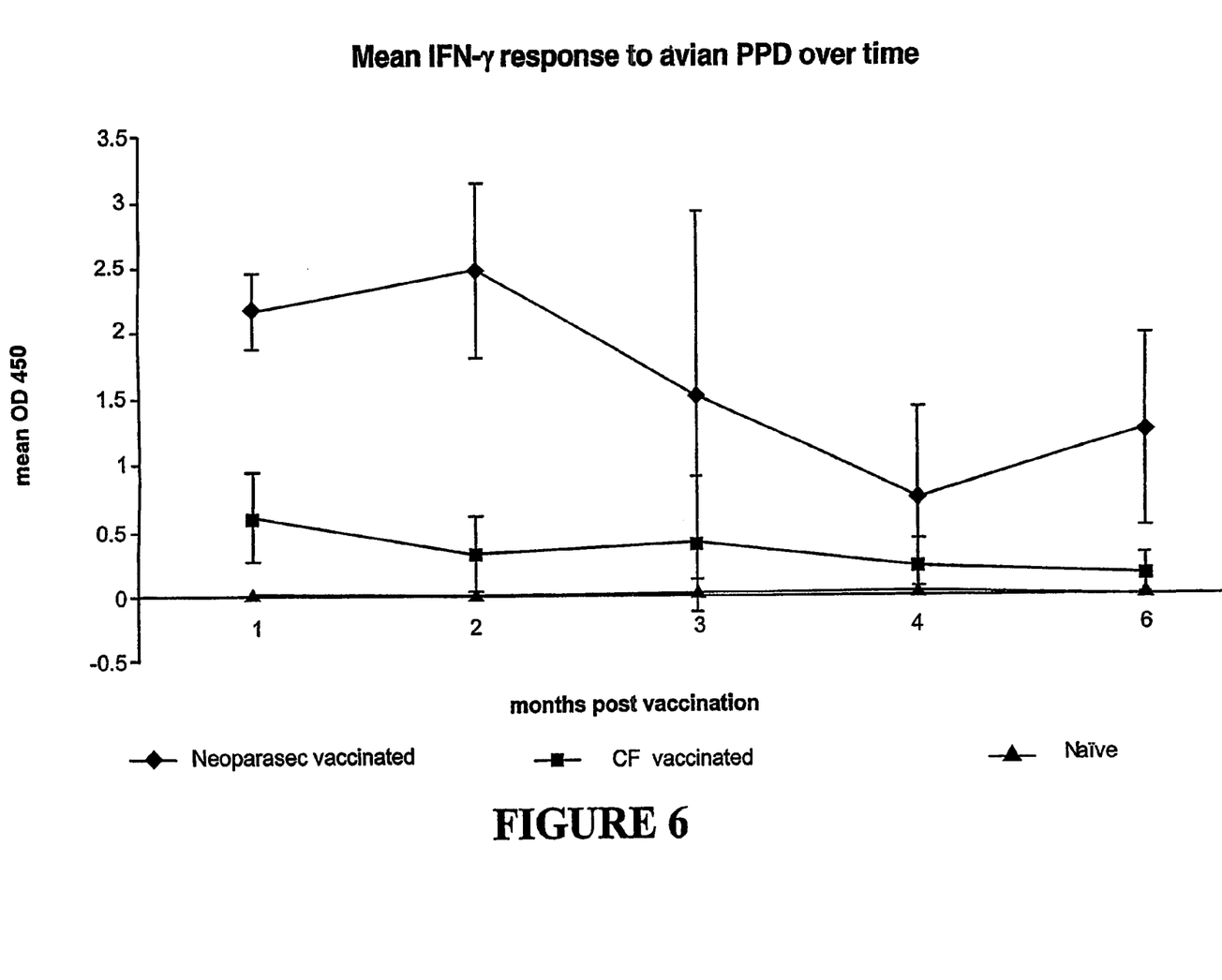
FIG. 6 is a graph of mean interferon gamma response to Avian PPD against the number of months after vaccination.
Figure 7:
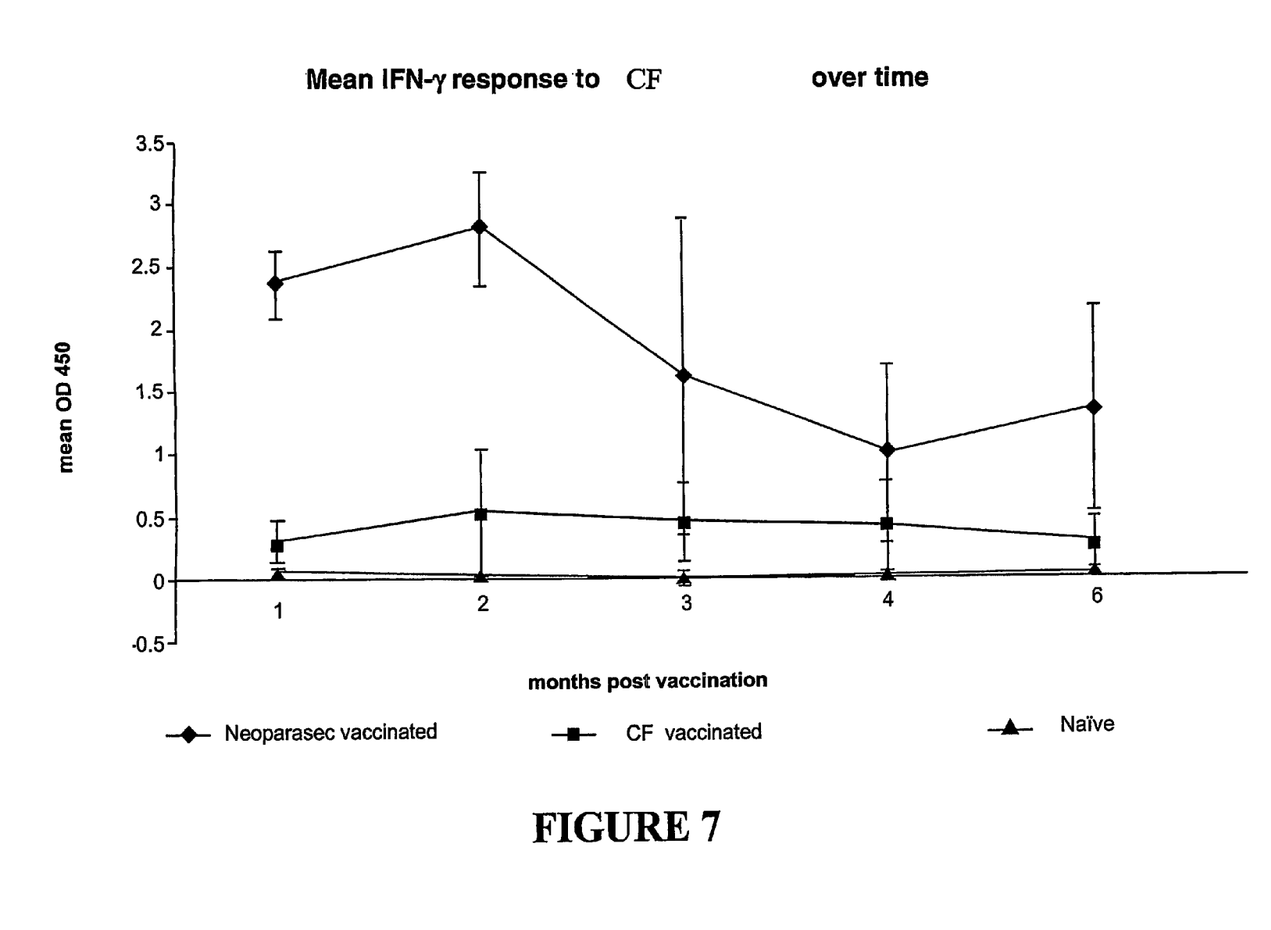
FIG. 7 is a graph of mean interferon gamma response to CF against the number of months after vaccination.

After 1, 2, 3, 4 and 6 months blood was collected from each of the animals. These monthly blood samples were tested for gamma interferon production by lymphocytes as a measure of cell-medium (protective immune response) to Avium PPD, Johnin PPD and CF M (75 μg CF per 1 ml of sheep blood). The result showed that immunization with Neoparasec gave a high response in all the in vitro tests for all the animals. The animals which were unvaccinated or vaccinated with media plus NPA gave samples which showed very little interferon production in response to PPD or CF M. An intermediate response was shown in the animals which had been vaccinated with CF plus NPA. The results for the 1 month assay are shown in FIG. 4. Similar results were shown in the blood samples over the following four months (not shown). FIG. 5 shows that even 6 months after vaccination, there is an interferon production response to Johnin PPD and CF. The time course of the response to Avian PPD and CF is shown in FIGS. 6 and 7 respectively.

The injection site lesions were scored at 0.5, 1, 2, 3 and 4 months post injection. At the 0.5 month examination the CF plus NPA group had the highest mean score of the four groups (including those treated with the live vaccine Neoparasec). At all subsequent examinations the mean scores for the CF plus NPA group had fallen below those for the Neoparasec group, but remained higher than for the group receiving media+NPA and the unvaccinated group.

At 2 months post-vaccination, antibody levels were measured using Paracheck (Johne's Absorbed EIA for the determination of paratuberculosis, CSL Ltd). The antibody levels were significantly higher in both the Neoparasec-vaccinated and CF-vaccinated groups than in the naive animals.

The above Examples are illustrations of practice of the invention. It will be appreciated by those skilled in the art that the invention can be carried out with numerous modifications and variations. For example the vaccinations may use a variety of different adjuvants, the strain of bacterium used to prepare the secreted proteins may be varied and the secreted proteins may be fractionated.

The invention claimed is:

1. A method for vaccinating an animal against *Mycobacterium avium* subsp. *paratuberculosis* comprising administering to the animal a vaccine comprising secreted protein from *Mycobacterium avium* subsp. *paratuberculosis* (*M. ptb*), the vaccine comprising fewer than 1000 whole organisms per ml of that species, either dead or alive.

2. The method as claimed in claim 1 wherein the animal is a ruminant.

3. The method as claimed in claim 2 wherein the ruminant is a sheep.

4. The method as claimed in claim 1, wherein the secreted proteins are obtained from a culture of *M. ptb*.

5. The method as claimed in claim 1, wherein the microorganisms are of an attenuated strain.

6. The method as claimed in claim 5, wherein the strain is the Weybridge vaccine stain.

7. The method as claimed in claim 1, wherein the vaccine further comprises an adjuvant.

8. The method as claimed in claim 1, wherein the vaccine further comprises a serum albumin.

9. The method as claimed in claim 4, wherein the secreted protein are obtained from a microorganism culture, the microorganism being removed by centrifugation and subsequent filtration.

10. The method as claimed in claim 1, wherein the vaccine does not contain whole organisms of that species, either dead or alive.

* * * * *